US006569436B1

(12) United States Patent  
Le Gros et al.

(10) Patent No.: US 6,569,436 B1  
(45) Date of Patent: May 27, 2003

(54) METHOD OF USING A VACCINE

(75) Inventors: Graham Stephen Le Gros, Wellington (NZ); Charles Richard William Beasley, Wellington (NZ); John William Holloway, Southampton (GB); Klaus Erb, Wurzburg (DE)

(73) Assignee: The Malaghan Institute of Medical Research, Wellington (NZ)

( * ) Notice: Subject to any disclaimer, the term of this patent is extended or adjusted under 35 U.S.C. 154(b) by 0 days.

(21) Appl. No.: 09/166,174

(22) Filed: Oct. 5, 1998

(51) Int. Cl.$^7$ .................. A61K 39/04; A61K 39/35; C12N 1/12; C12N 1/00

(52) U.S. Cl. .............. 424/248.1; 424/275.1; 424/557; 435/253.1; 435/863; 514/826

(58) Field of Search .............. 424/248.1, 275.1, 424/557; 435/253.1, 863; 514/826; 600/529, 533, 538

(56) References Cited

U.S. PATENT DOCUMENTS

| 5,599,545 A | 2/1997 | Stanford et al. ......... 424/282.1 |
| 5,721,270 A | 2/1998 | Okudaira et al. ........... 514/450 |
| 5,721,351 A | 2/1998 | Levinson .................... 536/23.4 |
| 5,767,097 A | 6/1998 | Tam ............................. 514/43 |

FOREIGN PATENT DOCUMENTS

| WO | WO99/32634 | 7/1999 |
| WO | WO00/74715 | 12/2000 |

OTHER PUBLICATIONS

Burrows, B., "Diseases Associated with Airways Obstruction", in, Cecil Textbook of Medicine, 15th Ed., Beeson et al, eds., W.B. Saunders Co., Philadelphia, pp. 951–965, Jan. 1, 1979.*
Marshall, E., "Gene Therapy's Growing Pains", Science, vol. 269, pp. 1050–1055, Aug. 1995.*
Culver, K.W., et al, "Gene Therapy for Cancer", TIG, vol. 10, No. 5, pp. 174–178, May 1994.*
Hodgeson, C.P., "Advances in vector systems for gene therapy", Exp. Opin. Ther. Patents, vol. 5, No. 5, pp. 459–468, May 1995.*
Miller, N., et al, "Targeted vectors for gene therapy", FASEB J., vol. 9, pp. 190–199, Jan. 1979.*
Zhizhen et al, GUANGZHOU MEDICAL JOURNAL, 15(2), "Inactivated BCG injection in the management . . . ", pp. 1–4, 1984.
Yuxin et al, TIAN JIN MEDICINE, 3, "Consecutive 5–Year Observation of Predominant Deactivated . . . ", pp. 1–5, 1987.

Loubei et al, ACTA OF HU–NAN MEDICAL, 17, "Prophylactic Effect of BCG Vaccination on the . . . ", pp. 1–5, 1992.
Shirakawa et al, SCIENCE, vol. 275, "The Inverse Association Between Tuberculin . . . ", pp. 77–79, Jan. 3, 1997.
Rosenthal et al, JOURNAL OF ASTHMA RESEARCH, vol. 5, No. 4, "Aerogenic BCG Vaccination Against . . . ", pp. 309–321, Jun. 1968.
Alm et al, THE LANCET, vol. 350, "Early BCG vaccination and development of atopy", pp. 400–403, Aug. 9, 1997.
Erb et al, J. EXP. MED, vol. 187, No. 4, "Infection of Mice with Mycobacterium bovis–Bacillus . . . ", pp. 561–569, Feb. 16, 1998.
Middlebrook, ASTHMA, "Immunological Aspects of Airborne Infection: Reactions to Inhaled antigens", pp. 331–346, 1961.
Barclay et al, JOURNAL OF BACTERIOLOGY, vol. 94, No. 5, "Effects of Oil–treated Mycobacterial . . . ", pp. 1736–1745, Nov. 1967.
Bloom et al, TUBERCULOSIS: Chapter 31, "The BCG Experience: Implications for Future Vaccines . . . ", pp. 531–552, 1994.
Immunological Reviews, Sher et al, "Role of T–Cell Derived Cytokines in the Downregulation . . . ", pp. 183–204, 1992 #127.
Science Reports, vol. 275, Shirakawa et al, "The Inverse Association Between Tuberculin . . . ", pp. 77–79, Jan. 1997.
Journal of Immunology, Donckier et al, "IFN–γ Prevents Th2 Cell–Mediated Pathology Neonatal . . . ", pp. 2361–2368, vol. 153.
Journal of Immunology, Lack et al, "Nebulized IFN–γ Inhibits the Development of Secondary . . . ", pp. 1432–1439, 1996, vol. 157.
Journal of Immunology, Li et al, "Mucosal IFN–γ Gene Transfer Inhibits Pulmonary Allergic . . . ", pp. 3216–3219, 1996, vol. 157.
The Lancet, vol. 350, Alm et al, "Early BCG vaccination and development of atopy", pp. 400–403, Aug. 9, 1997.
Immunology, Wang et al, "Inhibition of an established allergic response to ovalbumin . . . ", pp. 307–313, 1998, vol. 93.

* cited by examiner

Primary Examiner—Rodney P Swartz
(74) Attorney, Agent, or Firm—Jacobson Holman PLLC (57) ABSTRACT

This invention is directed to methods of preventing or reducing the severity of asthma or the risk of development of same in an individual. The method relies on administration to the airways of the individual of an immunologically effective dose of a mycobacterium based vaccine. The mycobacteria are effective in inducing a Th1 type immune response in the individual.

5 Claims, 9 Drawing Sheets

METHOD OF USING A VACCINE

This invention relates to an improved method for reducing the severity of asthma and the risk of developing asthma.

BACKGROUND ART

Asthma is a chronic inflammatory disorder of the airways in which many cells play a role, including mast cells and eosinophils. In susceptible individuals this inflammation causes symptoms which are usually associated with widespread but variable airflow obstruction that is often reversible either spontaneously or with treatment, and causes an associated increase in airway responsiveness to a variety of stimuli.

Asthma can be inherited, is not contagious and may be chronic and persistent or occurring in the form of attacks which are periodic and usually at least partly reversible. Attacks vary in severity and frequency from person to person. Many factors may contribute to the development of asthma including exposure to inhaled allergens such as pollens, mold spores, house dust mites and animal dander. In an individual who has developed asthma, many stimuli can trigger asthma attacks including allergens, viral respiratory infections (colds or the flu), irritants in the air (smoke, air pollution, perfume), damp, cold weather, and strenuous exercise. In addition, anxiety and emotional stress can bring on and worsen the symptoms of asthma.

During an asthma attack the muscles around the bronchial tubes tighten and the linings of the bronchial tubes swell (become inflamed) and produce thick mucus decreasing the internal diameter of the tubes. These changes block the flow of air making it hard to breathe. When asthma is properly controlled the bronchial tubes are of normal size.

Asthma is a common disease among both children and adults. An estimated 7% of people in the United States have been diagnosed as asthmatic. The corresponding figure for New Zealand is about 10% (Burney, P. et al. 1996 Variations in the Prevalence of Respiratory Symptoms, Self-Reported Asthma Attacks, and Use of Asthma Medication in the European Community Respiratory Health Survey. *Eur. Respir. J.* 9:687–695). The occurrence of asthma in both Western and developing countries has increased markedly over the last 30 years. This relatively short time frame suggests that environmental rather than genetic factors are at work.

In most cases asthma is an atopic disorder in which the underlying process is due to an allergic response to common environmental allergens. This allergic response is a function of the immune system characterized by activation and recruitment of eosinophils to the lung causing the characteristic chronic swelling and inflammation of the airways that affects the breathing of sufferers.

The pharmaceutical treatment of asthma includes several different classes of drugs, including beta agonists, topical or oral steroids and theophyllines. If used appropriately such treatments may keep asthma symptoms from developing or relieve them when they are present. Beta agonists and theophyllines primarily act by relaxing the muscles surrounding the airways while steroids act to reduce (and even prevent) inflammation and mucus production. Other medications exist and more are being developed due to the growing interest in and concern over the prevalence, morbidity and mortality of asthma worldwide.

Asthma is known to be a disease of the immune system. It is known that the process leading to inflammation of the airways is mediated by the Th2 lymphocytes (Th2s) whose usual function is to act against parasites. These cells secrete the cytokines interleukin-4 (IL-4) and IL-5 leading to enhanced production of immunoglobulin E (IgE) by B cells and the generation and recruitment of eosinophils respectively. Activation of mast cells by allergens releases histamine and other mediating chemicals that trigger an acute inflammatory response, including mucus production intended to flush dying parasites off tissue walls. In asthma the enhanced mucus production merely hinders breathing further. Eosinophils release cytotoxins meant to kill invading parasites but in asthma merely result in inflammation and necrosis of the bronchial epithelium. The increased eosinophil population, localized recruitment and the resultant tissue damage are termed "eosinophilia."

The global increase in atopic disorders such as asthma, hay fever and eczema is inversely correlated with the decline in the extent of exposure to human diseases such as tuberculosis, measles and whooping cough. These diseases all illicit a characteristic Th1 type immune response, mediated by the Th1 lymphocytes (Th1s), which leads to heightened expression of the cytokine interferon-$\gamma$ (IFN-$\gamma$), a powerful suppressive mediator of Th2 activity. It has been suggested that the lack of exposure to such Th1 inducing infections increases the risk of developing atopy and that by inducing a Th1 type immune response it is possible to down regulate the Th2 response thus reducing the likelihood of developing atopic disorders such as asthma.

The need exists for an asthma treatment that modulates the immune system to reduce the risk of developing atopy, rather than the traditional treatment of responding with drugs to suppress or alter the symptoms once the disorder has developed or the sufferer is in the midst of an attack. An added benefit would be if such a treatment also has a similar inhibitory effect in a current sufferer of an atopic disorder to reduce the severity of their disease.

PRIOR ART

It has been shown that among Japanese school children of between 12 and 13 years of age there is a strong inverse correlation between delayed hypersensitivity to *Mycobacterium tuberculosis* and atopy. Positive tuberculin responses predicted a lower incidence of asthma, lower serum IgE levels and cytokine profiles consistent with a Th1 response. (Shirakawa, T. et al. 1997 The Inverse Association Between Tuberculin Responses and Atopic Disorder. *Science* 275:77–79).

Another study has shown that early subcutaneous (Bacillus Calmette-Guérin [BCG]) infection in Swedish children with atopic heredity has no preventative effect on the development of atopic disorders before school age. (Alm, J. S. et al. 1997 Early BCG Vaccination and Development of Atopy. The Lancet 350:400–403).

*Mycobacterium vaccae* infections have been shown to suppress serum IgE and allergen-specific IL-5 synthesis in mice allergic to ovalbumin. (Wang, C. C. & Rook, G. A. W. 1998 Inhibition of an Established Allergic Response to ovalbumin in BALB/c Mice by killed *Mycobacterium vaccae*. *Immunology* 93: 307–313.)

U.S. Pat. No. 5,599,545 discloses an adjuvant consisting essentially of killed cells of *Mycobacterium vaccae* to be used in the immunotherapy of mycobacterial diseases such as tuberculosis and leprosy by promoting the Th1 response.

U.S. Pat. Nos. 5,767,097, 5,721,351 and 5,721,270 disclose various methods for inhibiting the Th2 response. However, they all refer to ways of interfering with an activated Th2 response rather than trying to prevent its activation or mediating it at a causal level.

OBJECT OF THE INVENTION

Therefore it is an object of this invention to provide a method for reducing the risk of the development of asthma in non-sufferers, and for reducing the severity of asthma in sufferers, by stimulating the body's immune system to suppress the atopic (Th2) immune response.

SUMMARY OF THE INVENTION

Accordingly one form of the invention may be said to be a method for reducing the severity of asthma and for reducing the risk of developing asthma, comprising
administering a vaccine
consisting of an immunologically effective dose of Th1 type immune response inducing mycobacteria
to the airways of individuals.

Preferably the vaccine is administered to the respiratory tract.

Preferably the vaccine consists of *Mycobacterium bovis* (Bacillus Calmette-Guérin [BCG]).

Preferably the vaccine contains $\geq 2\times10^5$ colony forming units (CFUs) of mycobacteria.

Preferably the vaccine contains $\geq 2\times10^5$ colony forming units (CFUs) of live mycobacteria.

Preferably the vaccine contains $\geq 2\times10^5$ colony forming unit (CFU) equivalents of killed mycobacteria.

Preferably the vaccine contains $\geq 2\times10^5$ colony forming unit (CFU) equivalents of mycobacterial cell wall components.

Preferably the vaccine contains $\geq 2\times10^5$ colony forming unit (CFU) equivalents of mycobacterial cell membrane components.

Preferably the vaccine contains $\geq 2\times10^5$ colony forming unit (CFU) equivalents of mycobacterial cell cytoplasm components.

Preferably the vaccine contains $\geq 2\times10^5$ colony forming unit (CFU) equivalents of mycobacterial genetic material.

Preferably the vaccine contains $\geq 2\times10^5$ colony forming unit (CFU) equivalents of mycobacterial secreted products.

BEST MODE OF PERFORMING THE INVENTION

The present invention offers a method of suppressing the development of airway eosinophilia and thus asthma via introduction to the airways of Th1 immune response inducing *Mycobacterium bovis* (Bacillus Calmette-Guérin [BCG]).

An "atopic" Th2 type immune response was induced in the lungs of mice either by ovalbumin (OVA) challenge after OVA immunization/sensitization or by infection with the helminth *Nippostrongylus brasiliensis*. In both cases the immune response was characterized by the accumulation of eosinophils into the airways and increased IgE levels in blood serum corresponding with the appearance of airway hyper responsiveness. When mice were infected intranasally with BCG leading to induction of a local Th1 immune response in the lung it was found that the BCG infection strongly inhibits the development of the Th2 type immune response and airway eosinophilia and that this effect was dependent on IFN-γ signaling.

It was found that the closer in time the BCG infection was to OVA challenge, the greater the degree of suppression of eosinophil accumulation in the airways. The inhibition of eosinophil accumulation in the airways correlated with a reduction in the capacity of draining lymph node cells to produce IL-5 upon in vitro re-stimulation with a purified protein derivative (PPD) of BCG. The stronger the inhibition of airway eosinophilia, the less IL-5 could be detected.

The inhibitory effect of BCG on airway eosinophilia was found to be dependent on the dose of infection with BCG numbers $\geq 2\times10^5$ colony forming units (CFUs) resulting in maximal inhibition. The route of infection also influenced BCG-induced suppression of airway eosinophilia with intranasal infection being superior to intraperitoneal or subcutaneous infection.

Homozygous IFN-γ knockout mice were used to investigate whether IFN-γ was the Th1-related cytokine responsible for the observed inhibition of airway eosinophilia. IFN-γR$^{-/-}$ mice receiving both the OVA immunization protocol and infection with BCG developed profound airway eosinophilia indicating that the BCG-induced inhibition was mediated by IFN-γ. However, the level of eosinophilia in the IFN-γR$^{-/-}$ mice infected with BCG was somewhat lower than that detected in mutant mice only subjected to the OVA immunization protocol. This indicates that other factors besides IFN-γ may play a role in the observed BCG mediated inhibition of airway eosinophilia. These data suggest that chronic inducers of IFN-γ expression generally lead to the inhibition of Th2 immune responses in vivo. The most likely explanation for the results is that the production of IFN-γ during an active BCG infection blocks the expansion of Th2s secreting IL-5 in the lung. The mechanism of IFN-γ induced inhibition is yet to be defined, but could involve activation of macrophages, switching of Th2 development or affecting dendritic cell activation and antigen presentation. Alternatively, the BCG invention could directly interfere with the homing of Th2s into the lung. Irrespective of the underlying mechanism, reduction of IL-5 production in the lung seems to be one of the major factors responsible for the observed inhibition of airway eosinophilia, since accumulation of eosinophils into the airways is highly dependent upon IL-5 and administration of IL-5 into the lung at least partly restores airway eosinophilia to 20–25% of the levels observed in control mice. However, since IL-5 administration into the lung did not totally restore eosinophil accumulation into the airways, it cannot be ruled out that the BCG infection also induced the production of some unknown factor thus contributing to the observed suppression of airway eosinophilia.

An important therapeutic implication of the invention is that the suppressive effect of BCG infection on the OVA-specific Th2 response was localized to the lung and did not influence blood eosinophil or OVA-specific IgG1 or IgE serum levels. This demonstrates that intranasal inoculation with BCG only suppressed the local Th2 immune response induced after OVA airway challenge and not the systemic one induced by the intraperitoneal immunization with OVA as an alum adjuvant.

Experiments with *N. brasiliensis* indicate that the suppressive effect of a BCG infection on airway eosinophilia can at least in part be overridden by the induction of a strong Th2 response.

The data demonstrates that a localized BCG infection in the lungs of mice can inhibit the accumulation of eosinophils into the airways and reduce the amount of IL-5 secreted by the T cells from the mediastinal lymph nodes and that the inhibitory effect was at least to a great degree dependent upon IFN-$\gamma$ signaling and could be partially reversed by the presence of IL-5 in the lung. BCG administration directly to the lung may potentially help in reducing the risk of developing severe asthma with the advantage of having little effect on the systemic immune response.

Experiments with killed BCG indicate that killed BCG can also inhibit airway eosinophilia. An important conclusion which can be made from this data is that the cellular constituents of *Mycobacterium bovis* (BCG) which could include: (1) cell wall, (2) cell membrane, (3) cell cytoplasm, (4) genetic material and (5) secreted products could be used to suppress airway eosinophilia.

The following Examples illustrate the invention:

EXAMPLE 1

Figure 1A:
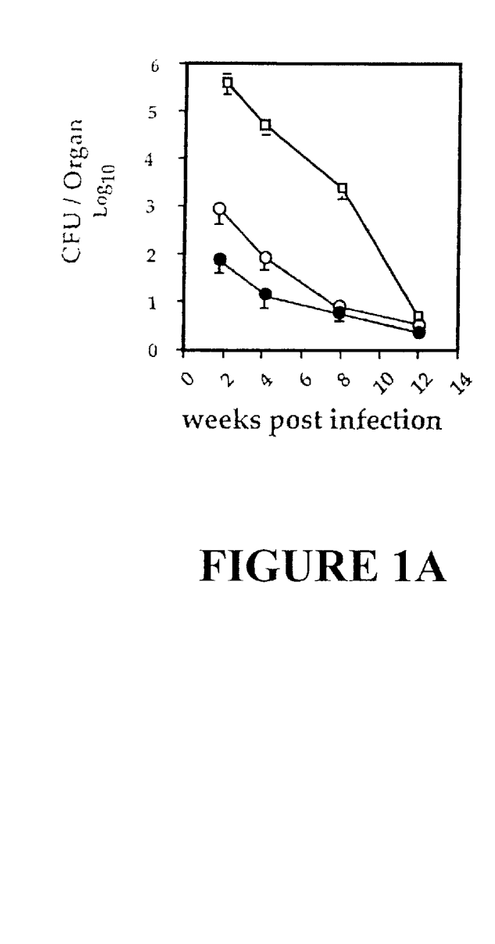
FIGS. 1A–1C illustrate that intranasal infection of mice with BCG induces a Th1 response in the lung.

Intranasal Infection of Mice with BCG leads to a Polarized Th1 Immune Response in the Lung An intranasal infection model was established to investigate whether Th1 immune responses would reduce the development of Th2 responses in the lung. Mice were anesthetized and intranasally inoculated with different infectious doses of BCG. Two-three weeks after intranasal infection with $2\times10^3$, $2\times10^4$ or $2\times10^5$ CFUs of BCG, distinct granulomas could be detected within tissue sections from lungs. At doses $>5\times10^5$ CFUs, small granulomas were also detected in the liver and spleen (data not shown.) FIG. 1A shows that mice intranasally infected with $2\times10^5$ CFUs of BCG cleared the mycobacteria from the lung (open squares), liver (open circles) and spleen (closed circles) during the following weeks with only a few persisting mycobacteria present after 12 weeks post-infection. Data shown are the mean bacterial counts of tissues from 9 mice (three separate experiments) with standard deviations.

Figure 1B:
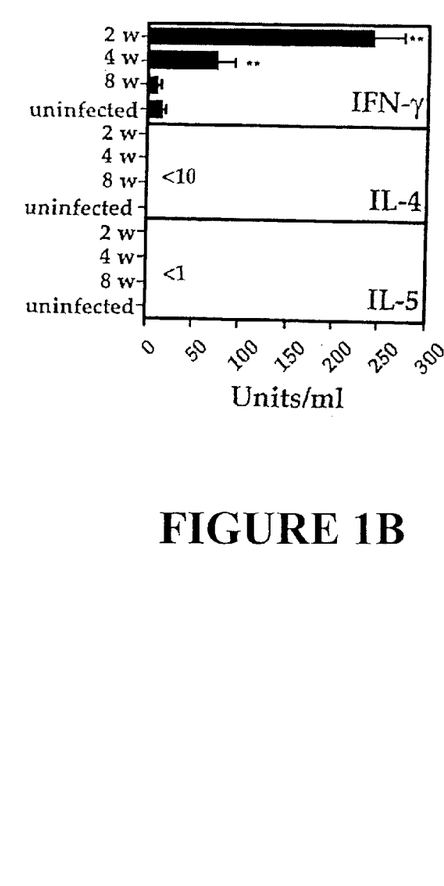

After 2, 4, and 8 weeks post-infection, cells isolated from the mediastinal lymph nodes of killed mice were stimulated with PPD from *M. bovis*. The antigen-specific activation with PPD only resulted in the detection of IFN-$\gamma$ with no IL-4 or IL-5 being detected, as shown in FIG. 1B. The data in FIG. 1B represent mean values of three separate experiments with standard deviation (from each experiment lymph nodes from three mice in each group were pooled.) Single-cell suspensions ($2\times10^5$/well) from total mediastinal lymph node isolates of control and 2, 4 and 8 week post-infection mice were stimulated in vitro for 48 hours with PPD (10 $\mu$g/ml.) The level of cytokines present in the supernatants was determined using sandwich ELISAs.

Throughout these experiments, ELISA cytokine detection was performed using the following mAb, recognizing two different epitopes of the respective lymphokines: biotinylated rat anti-mouse IFN-$\gamma$ (AN-18.17.24) and unconjugated rat anti-mouse IFN-$\gamma$, (R4-6A2), biotinylated rat anti-mouse IL-5 (TRFK4) and unconjugated rat anti-mouse IL-5 (TRFK5), and biotinylated rat anti-mouse IL-4 (BVD6-24G2) and unconjugated rat anti-mouse IL-4 (BVD4-1D11).

Figure 1C:
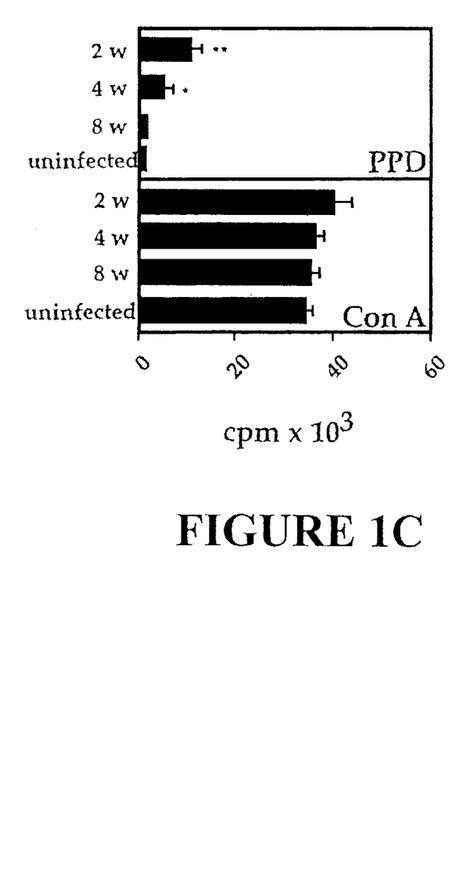

No IL-4 and only very low levels of IL-5 could be detected even after in vitro polyclonal T cell stimulation with anti-CD3 and IL-2 (data not shown). The T cell response to PPD was strongest after 2 weeks post infection and had subsided by 8–12 weeks post-infection as demonstrated by the kinetics of IFN-$\gamma$ production by T cells (FIG. 1B) and in vitro PPD-specific proliferation measured by [$^3$H]thymidine uptake by mediastinal lymphocytes (FIG. 1C). FIG. 1C shows [$^3$H]thymidine up-take by mediastinal lymphocytes of control and BCG-infected mice after stimulation with PPD or the lectin Con A. Lymph node cells ($2\times10^5$ cells/well) from uninfected and BCG-infected mice were incubated with medium, PPD (10 $\mu$g/ml) or Con A (5 $\mu$g/ml) for 40 hours and then pulsed with [$^3$H]thymidine for the last 16 hours of the culture period. Mean [$^3$H]thymidine uptake of triplicates with standard deviations are shown. Uptake of [$^3$H]thymidine was between 500 and 1,000 counts per million (cpm) in all cultures containing cells and medium alone.

The experiments detailed in FIGS. 1A, 1B and 1C were repeated 3 times with similar results [*$P<0.05$, **$P<0.0001$, compared to values obtained in cultures containing cells from uninfected mice—student's t test]. Taken together the results clearly demonstrate that intranasal infection with BCG induces a Th1 immune response in the lung.

EXAMPLE 2

Figure 2:
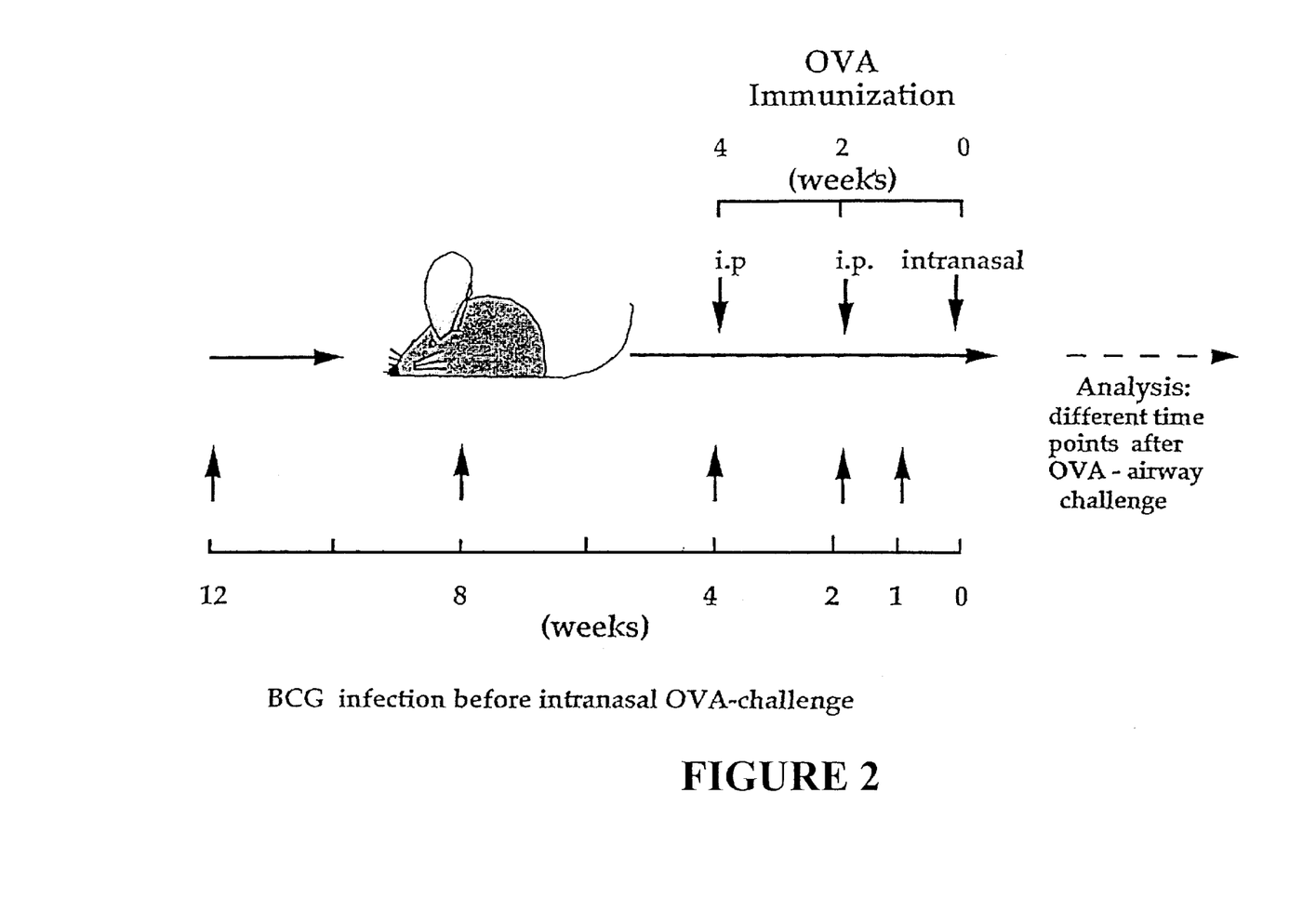
FIG. 2 illustrates the experimental design used to investigate the influence of a BCG infection on ovalbumin-(OVA)-induced eosinophilia in the lung following OVA immunisation.

BCG Infection in the Lung Strongly Suppresses the Development of OVA-induced Airway Eosinophilia To investigate the influence of a BCG infection on the development of an OVA-specific Th2 response in the lung an experimental protocol was developed in which BCG-infected and OVA-sensitized mice were airway challenged with OVA (FIG. 2.) Mice were sensitized by intraperitoneal injection with 2 $\mu$g OVA in 100 $\mu$l alum adjuvant on day 0 and boosted again intraperitoneally with 2 $\mu$g OVA/alum at day 14. Fourteen days after the second intraperitoneal immunization mice were anesthetized by injection of a mixture of Ketamine and Xylazine, and 100 $\mu$g OVA in a 50 $\mu$l volume of PBS (Phosphate Buffered Saline) was administered by intranasal inoculation. Intranasal infections were preformed using $2\times10^5$ CFUs of BCG as this dose results in a strongly polarized infection in the lung, but does not cause systemic disease.

Figure 3:
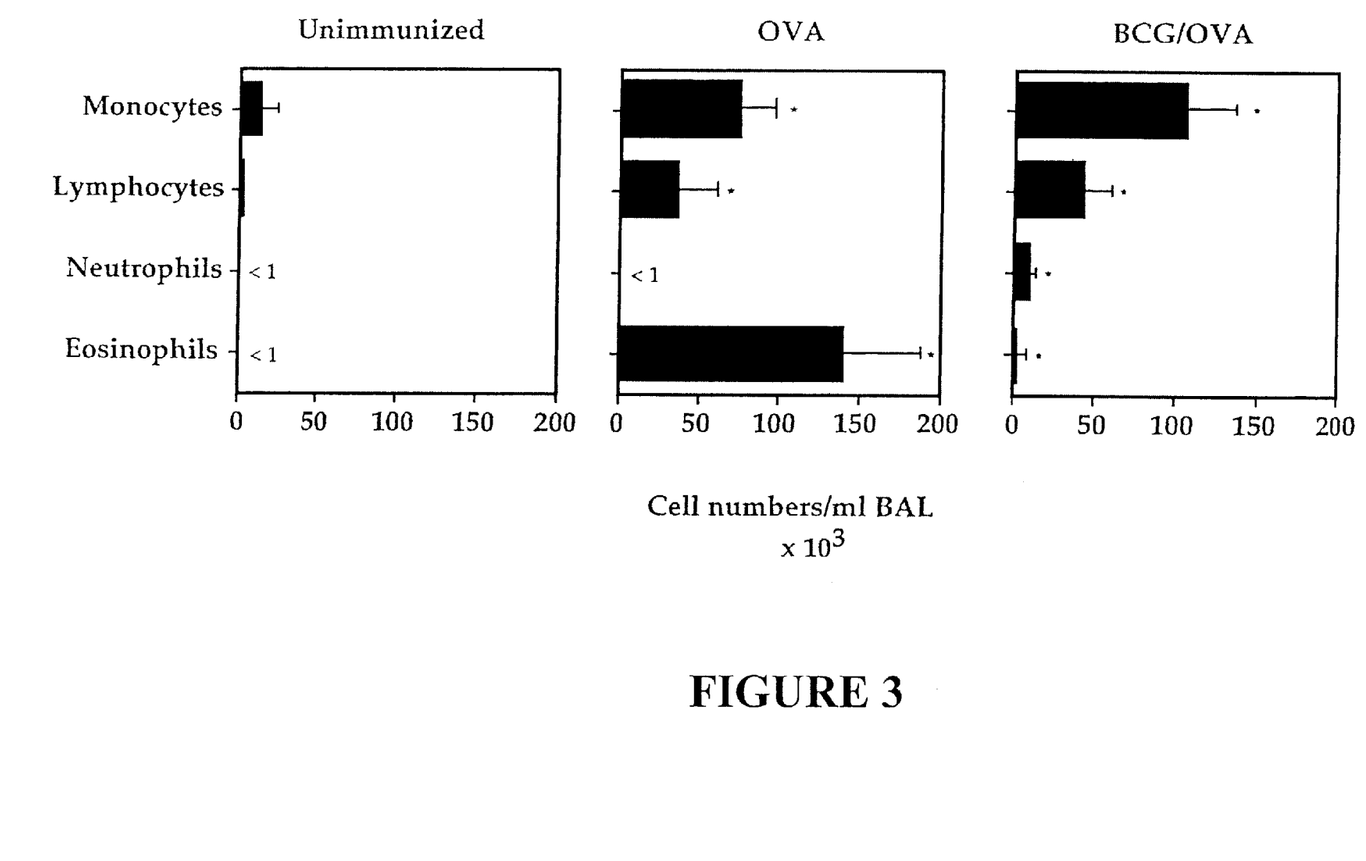
FIG. 3 illustrates that intranasal infection of BCG strongly inhibits the development of airway eosinophilia both (1) before T cell sensitization to OVA occurs and (2) after T cell sensitization, but before intranasal challenge. It is likely that BCG could also inhibit the development of airway eosinophilia after intranasal challenge.
Figure 4A:
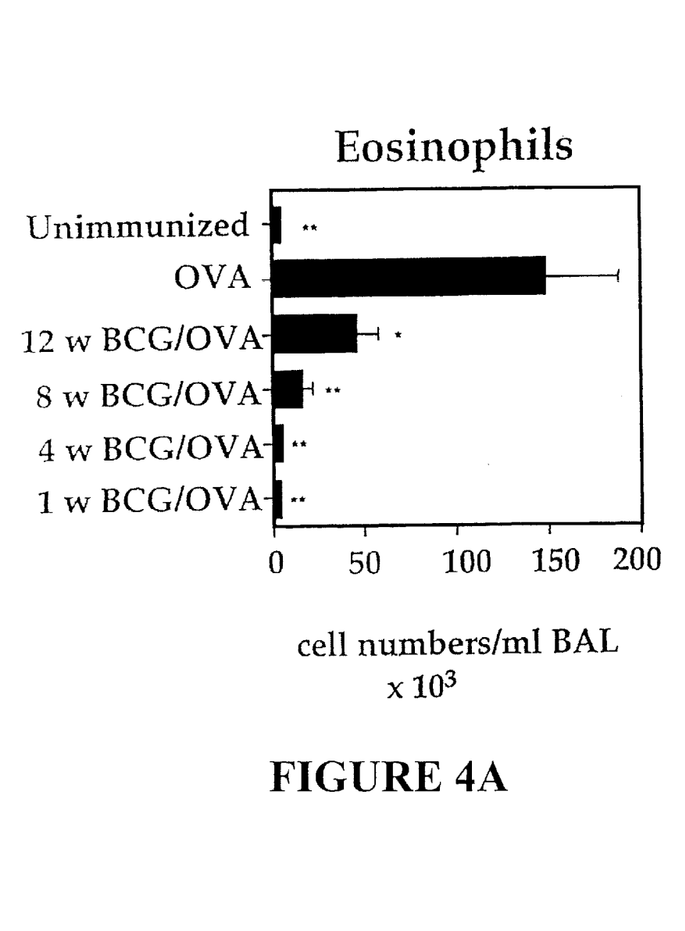
FIGS. 4A and 4B illustrate that intranasal infection of BCG strongly inhibits the development of airway eosinophilia but is dependent on the elapsed time from BCG infection before OVA challenge.

A BCG infection 4 weeks before OVA airway challenge had a profound suppressive effect on the allergen-induced accumulation of eosinophils into the lung as shown in FIG. 3. OVA-immunized mice were either intranasally infected with 2×10⁵ CFUs of BCG 4 weeks before OVA airway challenge or left uninfected as an OVA control. Six days after the OVA airway challenge, a bronchoalveolar lavage (BAL) was performed on both groups of mice as well as unimmunized mice. For all BALs, mice were killed, blood smears prepared, the trachea cannulated, and BALs performed by flushing lung and airway three times with 1 ml phosphate buffered saline (PBS). BAL cells were counted and spun onto glass slides and together with blood smears were stained and the percentages of macrophages, lymphocytes, neutrophils and eosinophils were determined microscopically using standard histological criteria. In FIG. 3 BAL cells were stained with haematoxylin and eosin. Shown are the average numbers of cells, with the standard deviation, present in the BALs of the different groups of mice (five mice per group). The experiments were repeated five times with similar results. [*$P<0.01$, compared to values obtained in unimmunized mice.] An increase in neutrophils, lymphocytes and monocytes in the BAL fluid of BCG-infected animals accompanied the decrease in eosinophils. Histological examinations of lung tissue from mice treated with BCG and OVA or OVA alone confirmed the strong reduction in lung eosinophil numbers after BCG infection (data not shown). The closer the time of BCG infection was to the OVA airway challenge, the more pronounced the suppressive effect was on lung eosinophilia as shown in FIG. 4A. OVA-immunized mice were either subjected to BCG infection at 1, 4, 8, or 12 weeks before OVA airway challenge or left unimmunized. Age-matched mice not subjected to the OVA immunization were included as controls. Six days after OVA airway challenge, BALs were performed on each group of mice. Shown in FIG. 4A are the average numbers of eosinophils present in the BALs of the different groups (n=5 for each group) of mice. Interestingly, even 12 weeks past the first infection, a suppressive effect on eosinophil accumulation into the lung could be observed.

Figure 4B:
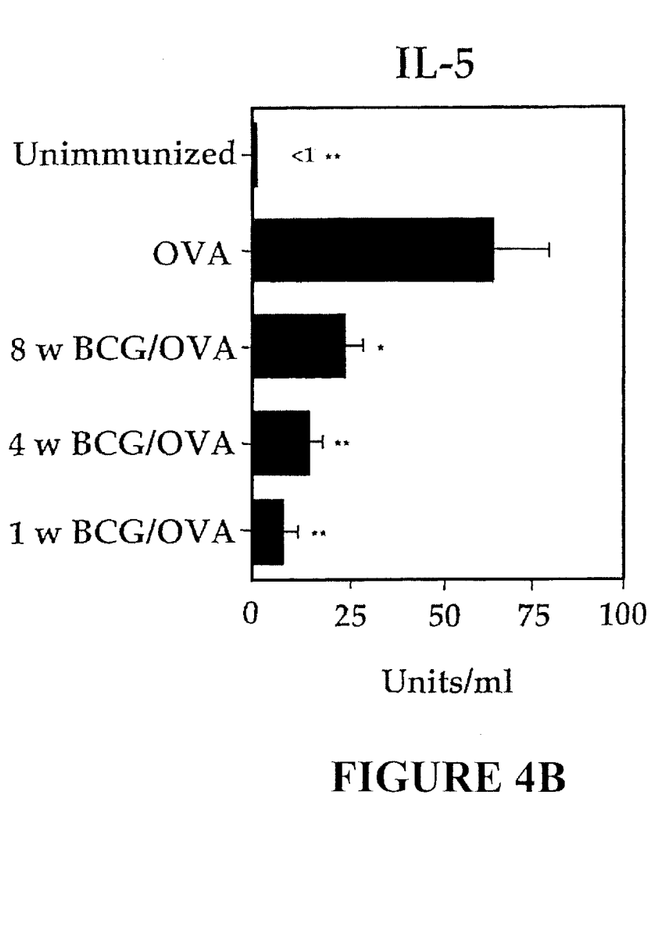

Eosinophil recruitment and development is dependent on the secretion of IL-5. Therefore, it was investigated whether the BCG induced suppression of airway eosinophilia was accompanied by reduction of Th2s producing IL-5 in the lung. It was found that BCG infection 1, 4, or 8 weeks before OVA challenge resulted in marked reduction in IL-5 production by restimulated T cells fro the draining lymph node. FIG. 4B shows these results where, in parallel to the BALs depicted in FIG. 4A, single-cell suspensions (2×10⁵ cells/well) from mediastinal lymph nodes of the different groups of mice were prepared and stimulated in vitro for 48 hours on anti-CD3-bound plates in the presence of IL-2. Shown is the amount of IL-5 present in the mediastinal lymph node cultures from three individual mice per group with standard deviation. [*$P<0.05$, **$P<0.0001$, compared to values obtained in OVA only immunized mice.]

In the experiments shown in FIGS. 3 and 4, responses were measured 6 days after OVA challenge, since eosinophilia and T cell reactivation could readily be monitored at this time point. Eosinophil numbers and IL-5 production were similarly reduced when the response was analyzed 3 or 10 days after OVA challenge in mice infected with BCG 4 weeks before OVA airway challenge (data not shown). These data further establish that the observed reduction of airway eosinophilia and IL-5 production by T cells was not due to a shift in the kinetics of the OVA-induced Th2 response.

Figure 5A:
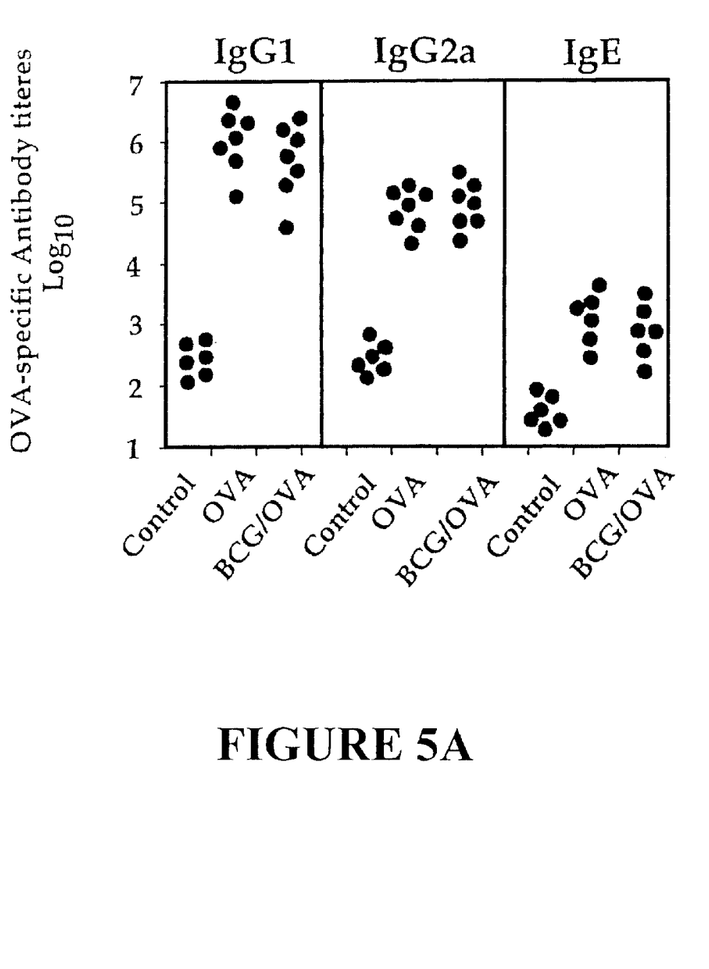
FIGS. 5A and 5B illustrate that BCG infection of the lung did not alter the development of OVA specific IgG1, IgG2a or IgE antibodies or blood eosinophilia.
Figure 5B:
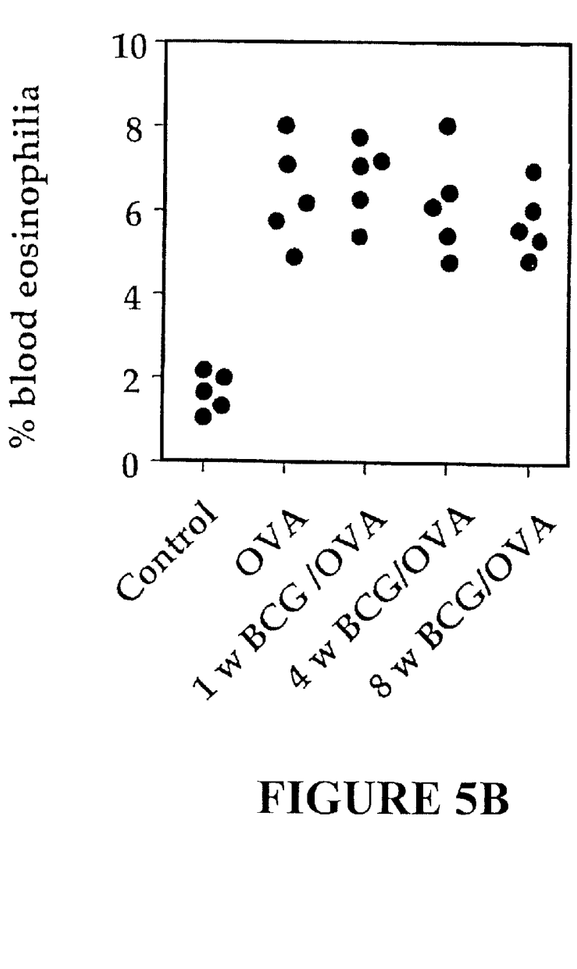

Even though BCG infection had a suppressive effect on both T cells secreting I1-5 and eosinophil accumulation into the airways, OVA-specific IgG1, IgG2a and IgE serum levels were not reduced or altered as shown in FIG. 5A. Serum and blood smears were prepared 10 days after OVA airway challenge (mice were treated as for FIG. 3) and OVA-specific antibody levels were determined by ELISA. The values in FIG. 3A represent serum antibody titres from the individual mice. Titres were determined by plotting $A_{414}$ against the logarithm of the reciprocal of the serum dilution and taking the midpoint of the linear section of the sigmoid curve produced. Blood smears were stained with hematoxylin and eosin and the different cell types were identified microscopically. In mice infected with BCG 1, 4 or 8 weeks before OVA challenge, blood eosinophilia was not reduced compared to mice only immunised with OVA as shown in FIG. 5B which shows the percentage of eosinophils present in the blood of individual mice. The control group in FIG. 5 was taken from age-matched uninfected mice.

EXAMPLE 3

BCG-induced Suppression of Airway Eosinophilia was Dependent upon IFN-γ Signaling and Could be Reversed by Intranasal Administration of IL-5

Figure 6A:
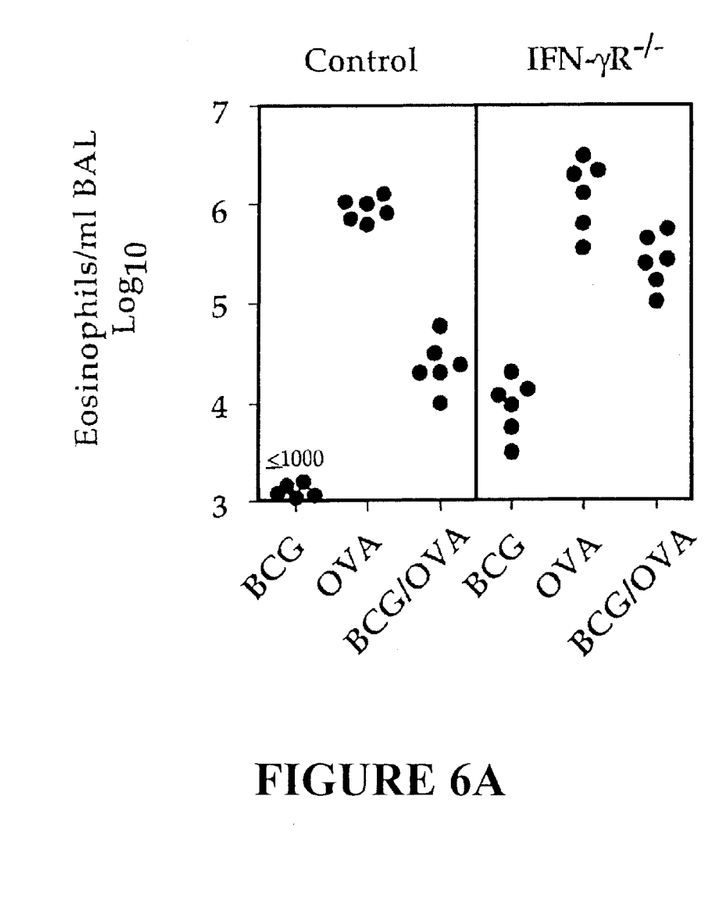
FIGS. 6A and 6B illustrate that BCG-induced suppression of airway eosinophilia was dependent upon IFN-γ mediated signals and could be reversed by the intranasal administration of IL-5.
Figure 6B:
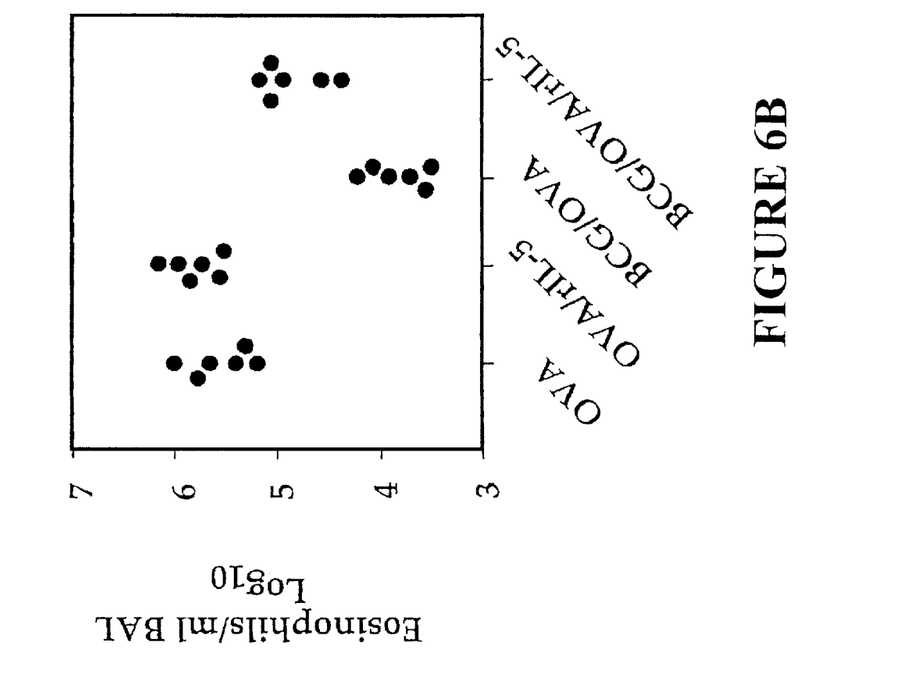

Previous research has shown that IFN-γ is able to inhibit the development of Th2 cell lines in vitro. To address the question of whether IFN-γ was mediating the observed inhibition of airway eosinophilia, IFN-γR$^{x/x}$ animals were subjected to the OVA immunization protocol and infected with BCG 2 weeks before OVA challenge. The deletion of the IFN-γR locus strongly reduced the BCG infection-induced inhibition of airway eosinophilia as shown in FIG. 6A. Twelve control (129/Sv/Ev) and 12 IFN-γR$^{x/x}$ mice were subjected to the OVA immunization protocol. From these mice, half were also infected with 2×10⁵ CFUs of BCG organisms 2 weeks before OVA airway challenge. Six days after intranasal OVA challenge, BALs were performed and numbers of eosinophils determined as described for FIG. 3. As controls, BALs were also prepared from non-OVA-immunized wild-type 129/Sv/Ev and IFN-γR$^{x/x}$ mice that had been infected with 2×10⁵ BCG organisms for 20 days. Shown are the numbers of eosinophils present in the BALs of six individual mice per group. As could be predicted, the IFN-γR$^{x/x}$ mice, but not controls develop a slight lung eosinophilia after BCG infection. Based on results obtained in the IFN-γR$^{x/x}$ mice, the most likely explanation for the results was that IFN-γ induced by the BCG infection in the lung suppressed the development of expansion of the Th2s specific for OVA and secreting IL-5. To rule out the possibility that the BCG infection directly interfered with eosinophil homing to the lung, it was investigated whether the intranasal administration of IL-5 could restore accumulation of eosinophils into the airways of OVA-primed and BCG-infected mice. The inhibitory effect of a BCG infection on OVA-induced airway eosinophilia could be partially reversed by intranasal administration of IL-5 to approximately 20–25% of the level observed in OVA only primed and airway challenged mice. This is shown in FIG. 6B where four groups of mice were subjected to the OVA immunization protocol, two of which were also intranasally infected with 2×10⁵ CFUs of BCG 4 weeks before OVA airway challenge. OVA-primed or OVA-primed and BCG-infected mice were either intranasally challenged with OVA or with a combination of OVA and IL-5 (500 units) and the numbers of eosinophils present in the BALs were determined 6 days after airway challenge. Shown are the numbers of eosinophils present in the BALs of six individual mice per group.

EXAMPLE 4

Reduction of Airway Eosinophilia was Dependent on the Dose of Mycobacteria Used and the Route of Infection In all the experiments outlined above, a standard dose of 2×10⁵ BCG organisms was used for the intranasal infections. To assess the number of BCG organisms necessary to induce the suppressive effect on the development of airway eosinophilia, mice were infected with different doses of BCG and subjected to the OVA immunization protocol. The use of $2\times10^6$ CFUs of BCG for infection 4 weeks before OVA challenge did not result in a higher degree of suppression than did a dose of $2\times10^5$ organisms. However, the suppressive effect was already markedly reduced using $2\times10^4$ and no longer detectable using $2\times10^3$ organisms as shown in FIG. 7A.

The inhibitory effect of BCG infection on the accumulation of eosinophils into the airways was dependent upon the route of infection. Intranasal infection was superior to intraperitoneal or subcutaneous infection in its ability to induce airway eosinophilia as shown in FIG. 7B using $2\times10^5$ CFUs of BCG.

Taken together, these experiments clearly demonstrate that the reduction in airway eosinophilia was both dependent on the amount of BCG organisms used and the route of infection.

Figure 7A:
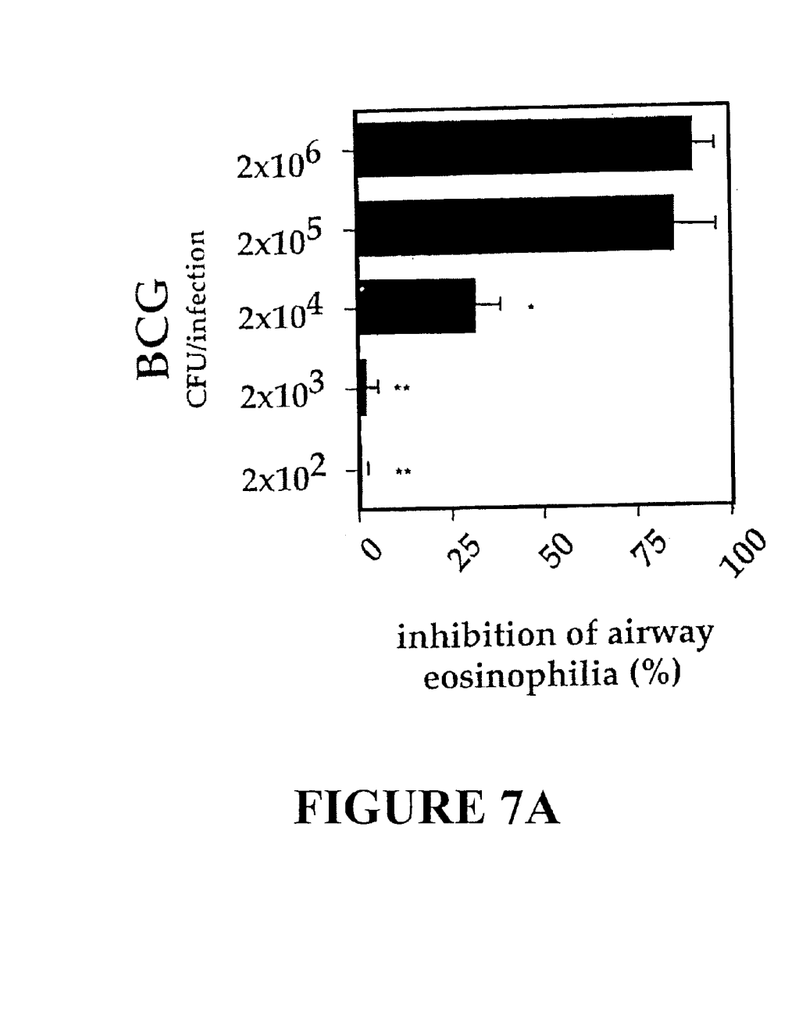
FIGS. 7A and 7B illustrate that inhibition of airway eosinophilia is both dependent on the dose and route of BCG infection.
Figure 7B:
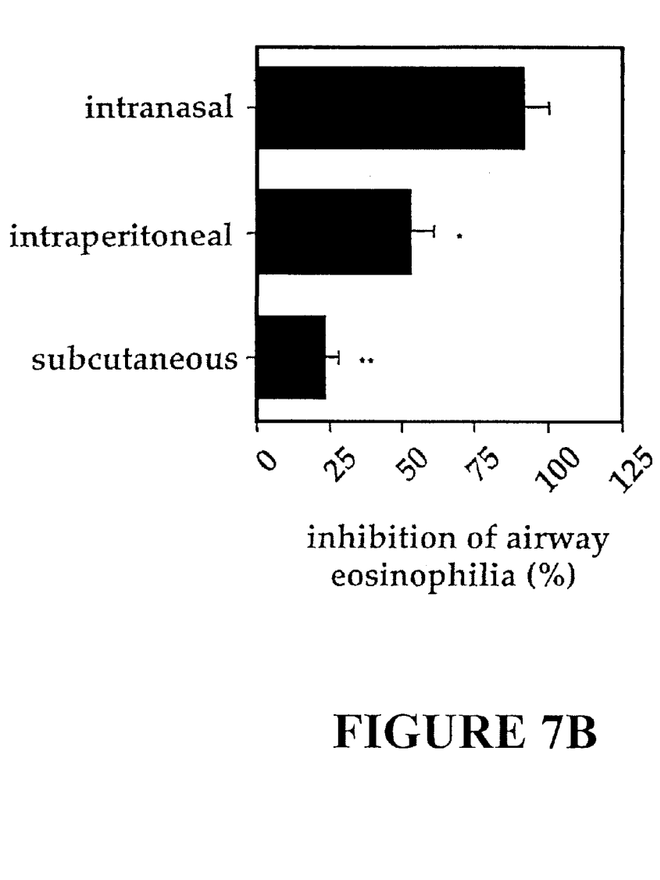

All of the infections displayed in FIG. 7 were performed 4 weeks before OVA challenge. Six days after OVA airway challenge BALs were prepared and treated as described for Example 2. Shown in FIG. 7 is the mean inhibition with standard deviation of the response from 5 age-matched mice. The experiments were repeated 3 times with similar results. [*$P<0.01$, **$P<0.0001$, compared to percentage of inhibition using $2\times10^6$ CFUs of BCG (7A) or intranasal infection (7B)].

EXAMPLE 5

Figure 8A:
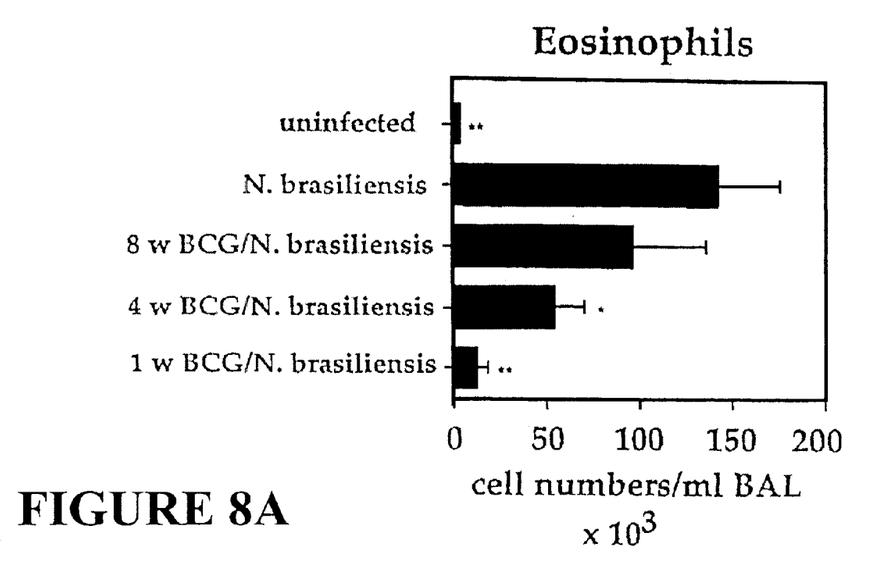
FIGS. 8A and 8B illustrate that intranasal infection with BCG reduces airway eosinophilia and the secretion of IL-4 and IL-5 by T cells after infection with the helminth *N. brasiliensis*.

BCG Infection in the Lung Partially Suppressed by the Development of Airway Eosinophilia Induced by *N. brasiliensis* Infection The Th2 response in the lung induced by the OVA immunization leads to the secretion of relatively low levels of IL-4 and IL-5 by T cells from the lung or mediastinal lymph nodes after in vitro stimulation (FIG. 4B and data not shown). It was next investigated whether BCG infections could also suppress the development of a strong natural Th2 response induced through infection with the helminth *N. brasiliensis*. Intranasal BCG infections were able to suppress accumulation of eosinophils into the lung after *N. brasiliensis* infection as shown in FIG. 8A. Mice were intranasally infected with $2\times10^5$ CFUs of BCG at the different time points indicated before intraperitoneal infection with 1,000 L3 larvae of *N. brasiliensis*. Ten days after *N. brasiliensis* infection, BAL and mediastinal lymph node cultures were prepared. Shown are the average numbers with standard deviations of eosinophils present in the BALs of five individual mice per group.

Figure 8B:
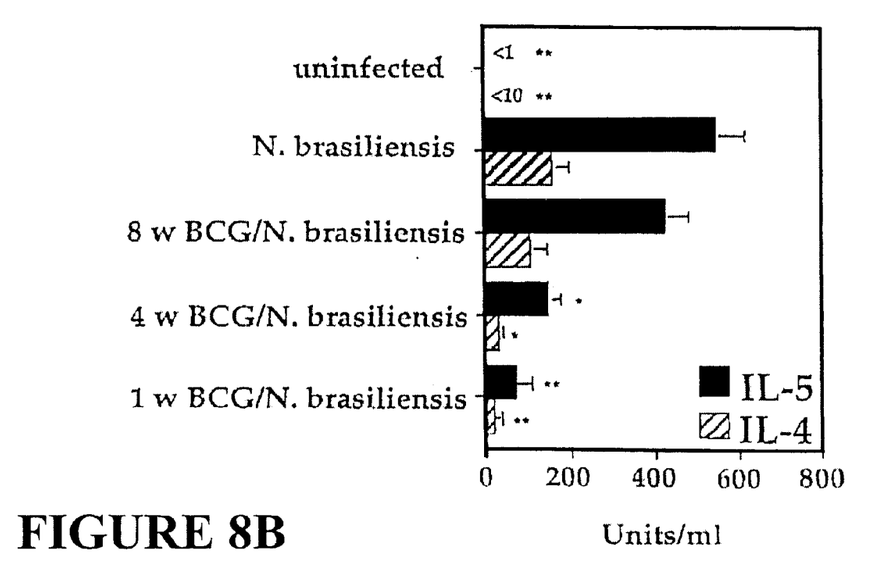

However, the accumulation of eosinophils into the lung was only strongly inhibited when the BCG infection was done 1 week before the *N. brasiliensis* infection. Infection with BCG before *N. brasiliensis* only reduced eosinophil numbers by approximately 50% and only 30% when performed 4 and 8 weeks before the helminth infection, respectively. The suppression of airway eosinophil accumulation correlated strongly with a marked reduction in IL-4 and IL-5 production by T cells from the mediastinal lymph nodes, measured after in vitro stimulation for 48 hours on anti-CD3-coated plates in the presence of IL-2 as shown in FIG. 8B. Shown is the mean amount of IL-4 and IL-5 produced by T cells in the mediastinal lymph node cultures from five individual mice per group with standard deviations. The experiments in FIGS. 8A and 8B were repeated 3 times with similar results. [*$P<0.01$, **$P<0.001$, compared to values obtained in cultures containing cells from mice only infected with *N. brasiliensis*].

It clearly appears that the closer the BCG infection was to that of *N. brasiliensis*, the less IL-4 and IL-5 could be detected in the cultures of T cells from the mediastinal lymph nodes.

Interestingly, the suppressive effect of a BCG infection on a developing Th2 response in the lung was more pronounced in the model of OVA-induced airway eosinophilia than after *N. brasiliensis* infection. This demonstrates that BCG infection can very efficiently inhibit the development of airway eosinophilia induced by allergens, but not as significantly as that induced by a helminth infection (FIGS. 4 and 8). These findings suggest that the amount of IFN-γ_ induced by infection with BCG is sufficient to suppress the relatively weak Th2 response induced by an OVA immunization but not the strong response induced by *N. brasiliensis* infection.

EXAMPLE 6

Intranasal Administration of Killed *Mycobacterium Bovis* BCG) Suppresses Development of OVA-Induced Airway Eosinophilia It was necessary to determine whether the suppressive effect of BCG on airway eosinophilia was dependent on active infection by live *Mycobacterium bovis* (BCG) or whether a killed form of BCG could also suppress airway eosinophilia. If the killed form of BCG was active in inhibiting airway eosinophilia it could be concluded that the cellular constituents of *Mycobacterium bovis* (BCG) potentially including cell wall, cell membrane, cell cytoplasm, genetic material and cell secreted products could inhibit airway eosinophilia by mechanisms similar to that outlined for live BCG.

Figure 9:
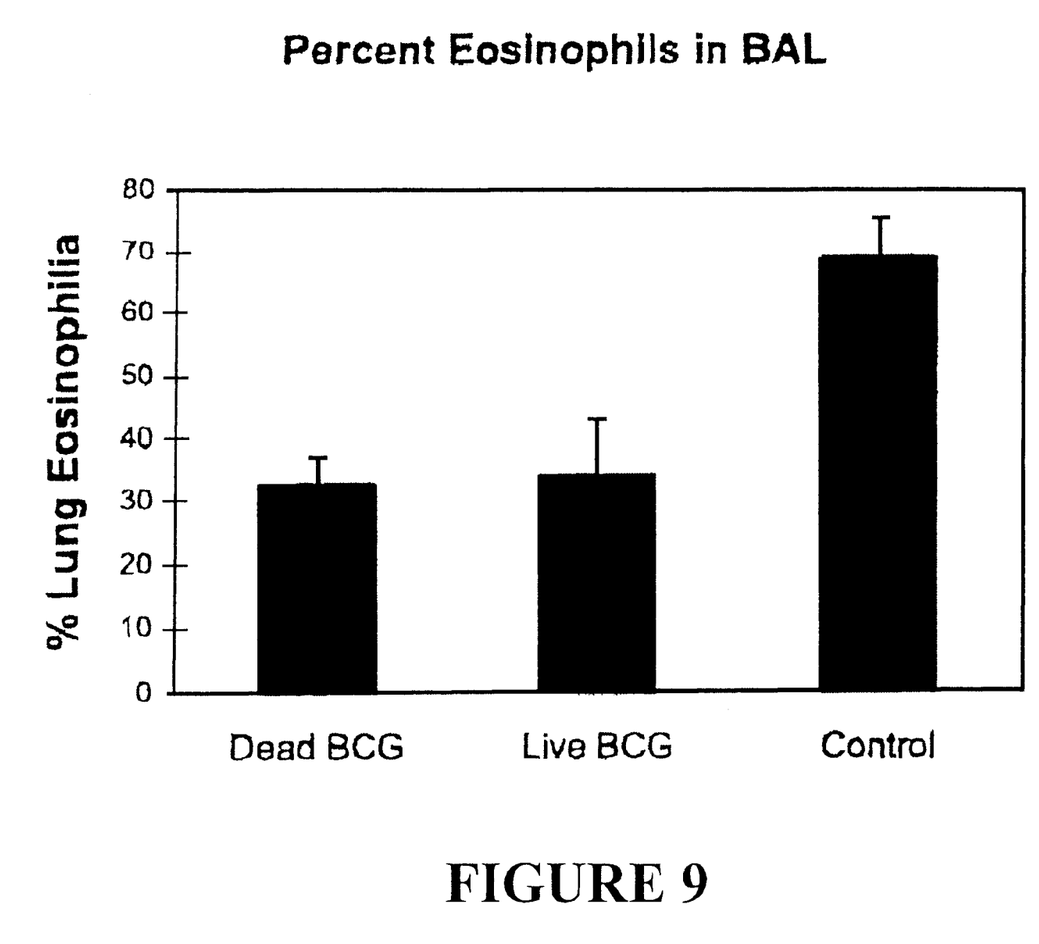
FIG. 9 illustrates that intranasal infection with killed (dead) BCG can suppress airway eosinophilia.

To address this question mice were sensitized by intraperitoneal injection with 2 μg OVA in 100 μl alum adjuvant on day 0 and boosted again intraperitoneally with 2 μg OVA/alum at day 14. Seven days following the second intraperitoneal injection with 2 μg OVA/alum groups of 8 mice received intranasal inoculation with either (1) $2\times10_5$ CFUs of live BCG, (2) $2\times10_5$ CFU equivalents of killed (dead) BCG (heated to 75 degrees celsius for 30 minutes— no viable bacteria detected), or (3) resuspension diluent control (FIG. 9). Seven days later all groups of mice received an intranasal inoculation of 100 μg OVA in a 50 μl volume of PBS. Six days after the OVA airway challenge, a bronchoalveolar lavage (BAL) was performed on all groups of mice, cells counted, stained and histologically scored as in Example 2. The results shown in FIG. 9 show that both killed (dead) BCG and live BCG significantly inhibited the OVA-induced airway eosinophilia when compared to the OVA-challenged control non-BCG treated mice. Taken together these data demonstrate that killed BCG can inhibit airway eosinophilia. An important conclusion, which can be made from this data, is that the cellular constituents of *Mycobacterium bovis* (BCG) which could include: (1) cell wall, (2) cell membrane, (3) cell cytoplasm, (4) genetic material and (5) secreted products could be used to suppress airway eosinophilia.

Having described preferred methods of putting the invention into effect, it will be apparent to those skilled in the art to which this invention relates, that modifications and amendments to various features and items can be effected and yet still come within the general concept of the invention. It is to be understood that all such modifications and amendments are intended to be included within the scope of the present invention.

What is claimed is:

1. A method for reducing the severity of asthma and for reducing the risk of developing asthma in a subject comprising treating allergen-induced airway eosinophilia by administering a vaccine consisting of an immunologically effective dose of Th1 type immune response inducing *Mycobacterium bovis* (BCG) to the airways of the subject.

2. The method of claim 1, wherein the vaccine is administered to the respiratory tract.

3. The method of claim 1, wherein the immunologically effective dose comprises about $2 \times 10^5$ colony forming units (CFUs) or more of *Mycobacterium bovis* (BCG).

4. The method of claim 3, wherein the *Mycobacterium bovis* (BCG) is killed.

5. The method of claim 3, wherein the *Mycobacterium bovis* (BCG) is live.

* * * * *